(12) United States Patent
Gray et al.

(10) Patent No.: US 10,856,882 B2
(45) Date of Patent: *Dec. 8, 2020

(54) OCCLUSION DEVICE

(71) Applicant: Boston Scientific Scimed, Inc., Maple Grove, MN (US)

(72) Inventors: Jeff Gray, Sudbury, MA (US); Nathan Zamarripa, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 218 days.

This patent is subject to a terminal disclaimer.

(21) Appl. No.: 15/914,937

(22) Filed: Mar. 7, 2018

(65) Prior Publication Data

US 2018/0193028 A1    Jul. 12, 2018

Related U.S. Application Data

(63) Continuation of application No. 14/615,051, filed on Feb. 5, 2015, now Pat. No. 9,987,014.

(Continued)

(51) Int. Cl.
*A61B 17/12* (2006.01)
*A61M 25/10* (2013.01)
(Continued)

(52) U.S. Cl.
CPC .. *A61B 17/12136* (2013.01); *A61B 17/12022* (2013.01); *A61B 17/12031* (2013.01); *A61B 17/12109* (2013.01); *A61M 25/104* (2013.01); *A61B 2017/00309* (2013.01); *A61B 2017/12054* (2013.01); *A61B 2017/12081* (2013.01); *A61M 25/007* (2013.01); *A61M 25/0052* (2013.01); *A61M 2025/0042* (2013.01); *A61M 2025/0059* (2013.01); *A61M 2025/0076* (2013.01); *A61M 2025/1052* (2013.01); *A61M 2025/1054* (2013.01)

(58) Field of Classification Search
CPC ........ A61B 17/12136; A61B 17/12022; A61B 17/12109; A61B 17/12031; A61B 2017/00309; A61B 2017/12081; A61B 2017/12054; A61M 25/104; A61M 25/0052; A61M 25/007; A61M 2025/0059; A61M 2025/1052; A61M 2025/0042; A61M 2025/0076; A61M 2025/1054

See application file for complete search history.

(56) References Cited

U.S. PATENT DOCUMENTS 4,085,757 A * 4/1978 Pevsner ........... A61B 17/12031
                                              604/907
4,282,875 A * 8/1981 Serbinenko ...... A61B 17/12109
                                              604/907

(Continued)

*Primary Examiner* — Phong Son H Dang

(57) ABSTRACT

A catheter includes a detachable tip assembly that when detached from the catheter may be used to occlude a body lumen or vessel. The detachable distal tip assembly may include an inflatable balloon disposed over and secured to a tubular member. The inflatable balloon may be in fluid communication within an inflation lumen extending within the catheter body. Upon reaching a target site within a body lumen or vessel, the detachable distal tip assembly may be released from the distal end of the catheter upon inflation of the balloon to a predetermined size.

20 Claims, 13 Drawing Sheets

Related U.S. Application Data

(60) Provisional application No. 61/936,653, filed on Feb. 6, 2014.

(51) Int. Cl.
*A61M 25/00* (2006.01)
*A61B 17/00* (2006.01)

(56) References Cited

U.S. PATENT DOCUMENTS

| | | | | |
|---|---|---|---|---|
| 4,364,392 A * | 12/1982 | Strother | A61B 17/0057 | 606/195 |
| 4,517,979 A * | 5/1985 | Pecenka | A61B 17/12109 | 604/907 |
| 5,261,916 A * | 11/1993 | Engelson | A61B 17/12022 | 606/108 |
| 5,304,195 A * | 4/1994 | Twyford, Jr. | A61B 17/12022 | 606/191 |
| 6,063,100 A * | 5/2000 | Diaz | A61B 17/12022 | 606/191 |
| 6,331,184 B1 * | 12/2001 | Abrams | A61B 17/12022 | 604/164.09 |
| 6,375,668 B1 * | 4/2002 | Gifford | A61B 17/12022 | 606/200 |
| 6,379,329 B1 * | 4/2002 | Naglreiter | A61B 17/12113 | 604/101.02 |
| 6,428,558 B1 * | 8/2002 | Jones | A61B 17/12022 | 606/151 |
| 6,849,081 B2 * | 2/2005 | Sepetka | A61B 17/12022 | 606/1 |
| 6,964,657 B2 * | 11/2005 | Cragg | A61B 17/12022 | 604/508 |
| 6,994,711 B2 * | 2/2006 | Hieshima | A61B 17/12022 | 606/108 |
| 7,695,488 B2 * | 4/2010 | Berenstein | A61B 17/12177 | 606/194 |
| 7,985,238 B2 * | 7/2011 | Balgobin | A61M 29/00 | 606/200 |
| 8,062,325 B2 * | 11/2011 | Mitelberg | A61F 2/95 | 606/200 |
| 8,523,902 B2 * | 9/2013 | Heaven | A61B 17/0401 | 606/232 |
| 8,900,304 B1 * | 12/2014 | Alobaid | A61B 17/7097 | 623/17.12 |
| 9,579,104 B2 * | 2/2017 | Beckham | A61B 17/12113 | |
| 2002/0068974 A1 * | 6/2002 | Kuslich | A61F 2/441 | 623/17.11 |
| 2002/0147497 A1 * | 10/2002 | Belef | A61F 2/4611 | 623/17.12 |
| 2003/0028209 A1 * | 2/2003 | Teoh | A61B 17/12172 | 606/191 |
| 2004/0210297 A1 * | 10/2004 | Lin | A61B 17/7097 | 623/1.11 |
| 2007/0167876 A1 * | 7/2007 | Euteneuer | A61M 25/09 | 600/585 |
| 2008/0103505 A1 * | 5/2008 | Fransen | A61B 17/7097 | 606/92 |
| 2009/0227983 A1 * | 9/2009 | Griffin | A61M 25/0068 | 604/526 |
| 2009/0287291 A1 * | 11/2009 | Becking | A61B 17/12118 | 623/1.11 |
| 2010/0069948 A1 * | 3/2010 | Veznedaroglu | A61B 17/12022 | 606/194 |
| 2011/0112588 A1 * | 5/2011 | Linderman | A61B 17/8855 | 606/86 R |
| 2011/0137317 A1 * | 6/2011 | O'Halloran | A61B 17/8855 | 606/92 |
| 2011/0152993 A1 * | 6/2011 | Marchand | A61B 17/12172 | 623/1.2 |
| 2012/0165732 A1 * | 6/2012 | Muller | A61B 17/8855 | 604/99.01 |
| 2012/0191123 A1 * | 7/2012 | Brister | A61M 25/10186 | 606/191 |
| 2013/0261658 A1 * | 10/2013 | Lorenzo | A61B 17/1214 | 606/200 |
| 2016/0249934 A1 * | 9/2016 | Hewitt | A61B 17/12177 | 606/200 |

* cited by examiner

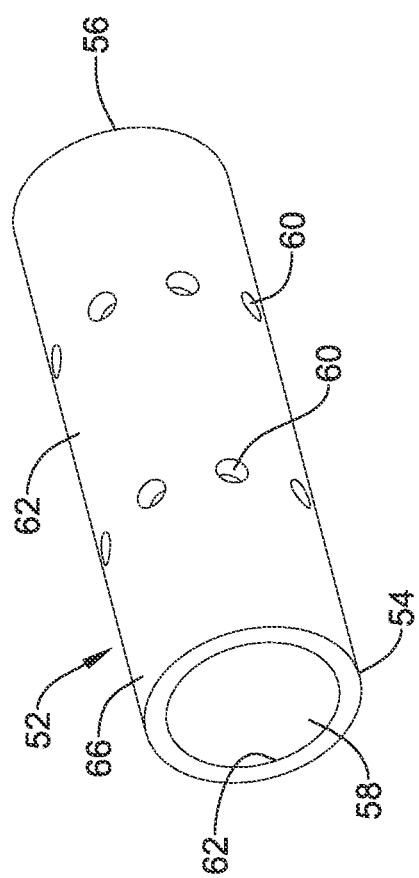

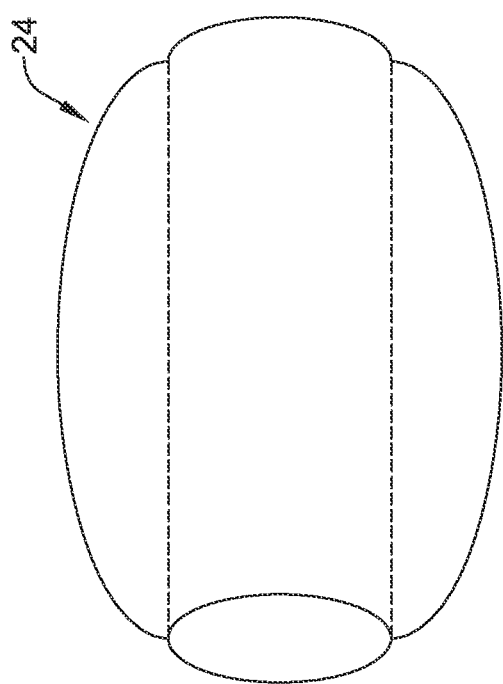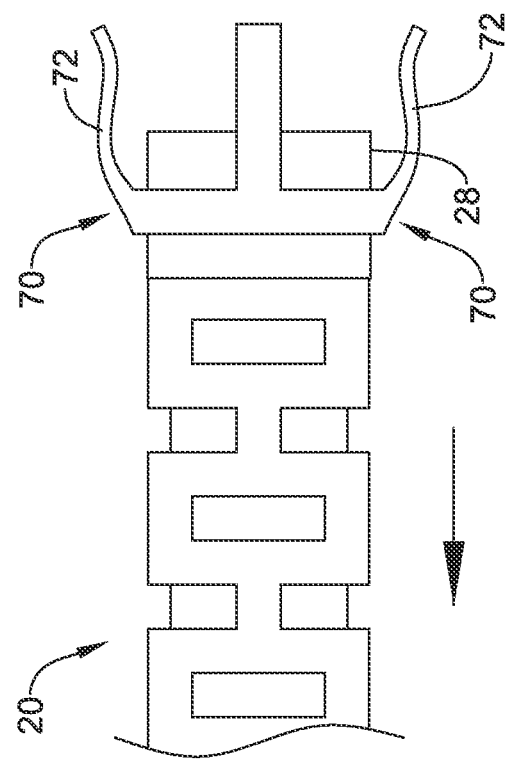
FIG. 7C

OCCLUSION DEVICE

CROSS-REFERENCE TO RELATED APPLICATIONS

This application is a continuation of, and claims the benefit of priority to, U.S. patent application Ser. No. 14/615,051, filed Feb. 5, 2015, which claims the benefit of priority under 35 U.S.C. § 119 to U.S. Provisional Application Ser. No. 61/936,653, filed Feb. 6, 2014, the disclosures of which are herein incorporated herein by reference in their entirety.

TECHNICAL FIELD

This disclosure relates to endovascular devices, and more particularly, to vaso-occlusive devices for the occlusion of body lumens and cavities.

BACKGROUND

In many clinical situations, blood vessels are occluded for a variety of purposes, such as to control bleeding, to prevent blood supply to tumors, and to block blood flow within an aneurysm. Vaso-occlusive devices have been used in the treatment of aneurysms. Vaso-occlusive devices are surgical implants placed within blood vessels or vascular cavities, typically by the use of a catheter, to form a thrombus and occlude the site. For instance, an aneurysm may be treated by introduction of a vaso-occlusive device through the neck of the aneurysm. The thrombogenic properties of the vaso-occlusive device cause a mass to form in the aneurysm and alleviate the potential for growth of the aneurysm and its subsequent rupture. Other diseases, such as tumors, may also be treated by occluding the blood flow to a target area.

SUMMARY

This disclosure relates to endovascular devices, and more particularly, to vaso-occlusive devices for the occlusion of body lumens and cavities. In one illustrative embodiment, a medical device can include: a main catheter body extending from a proximal end to a distal end; an inflation lumen extending within the main catheter body; a distal tip assembly releasably coupled to the distal end of the main catheter body; and a release mechanism coupled to the distal end of the main catheter body. In some embodiments, the distal tip assembly can include a tubular member defining a lumen extending from a proximal end to a sealed distal end, the tubular member including a plurality of apertures formed in an outer surface thereof, and an inflatable balloon disposed over and secured to the tubular member, and the release mechanism can include two or more retaining members extending distally away from the distal end of the main catheter body and engaging an outer surface of the inflatable balloon when the distal tip assembly is coupled to the distal end of the main catheter body prior to deployment. The retaining members can be configured such that upon expansion of the inflatable balloon, the retaining members are flexed outward and away from the main catheter body until the distal tip assembly including the inflatable balloon is released from the main catheter body.

In another illustrative embodiment, a catheter assembly includes: a catheter having an elongated catheter shaft including an outer tubular member having a plurality of apertures defined therein disposed over an inner tubular member, the inner tubular liner defining at least one lumen extending from a proximal end to a distal end of the inner tubular member, wherein a distal region including the distal end of the inner tubular liner extends beyond a distal end of the outer tubular member of the elongated catheter shaft; and an occlusion device releasably attached to the distal end of the outer tubular member of the catheter shaft. The occlusion device can include a tubular member defining a lumen extending from an open proximal end to a sealed distal end, the tubular member including a plurality of apertures formed in an outer surface thereof, and an inflatable balloon disposed over and secured to the tubular member.

In yet another illustrative embodiment a method of delivering an occlusion device to a target location within a lumen of a patient's body includes advancing a catheter assembly to a target location within the lumen of a patient's body. In some cases, The catheter assembly can include: an elongated catheter shaft including an outer tubular member having a plurality of apertures defined therein disposed over an inner tubular liner, the inner tubular member defining at least one lumen extending from a proximal end to a distal end of the inner tubular liner, wherein a distal region including the distal end of the inner tubular liner extends beyond a distal end of the outer tubular member of the catheter shaft; and an occlusion device releasably attached to the distal end of the outer tubular member of the catheter shaft. The occlusion device can include a tubular member defining a lumen extending from an open proximal end to a sealed distal end, the tubular member including a plurality of apertures formed in an outer surface thereof, and an inflatable balloon disposed over and secured to the tubular member. Additionally, the method can include inflating the inflatable balloon to at least a predetermined size, wherein inflation of the inflatable balloon to the predetermined size causes the occlusion device to be released from the distal end of the outer tubular member of the catheter shaft; and withdrawing the catheter shaft in a proximal direction away from the occlusion device to further release the occlusion device from the distal end of the catheter shaft. In other cases, the method can include controlling the inflation of the balloon such that that the inflatable balloon may be expanded to meet the required size of the vessel in which the balloon is deployed.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF THE DRAWINGS

The disclosure may be more completely understood in consideration of the following detailed description of various embodiments in connection with the accompanying drawings, in which:

FIG. 5 is a perspective view of a tubular member that forms a portion of a distal tip assembly in accordance with an embodiment of the present disclosure;

FIGS. 7A-7C show a distal tip assembly during different stages of detachment from a distal end of a catheter in accordance with an embodiment of the present disclosure;

Figure 1:
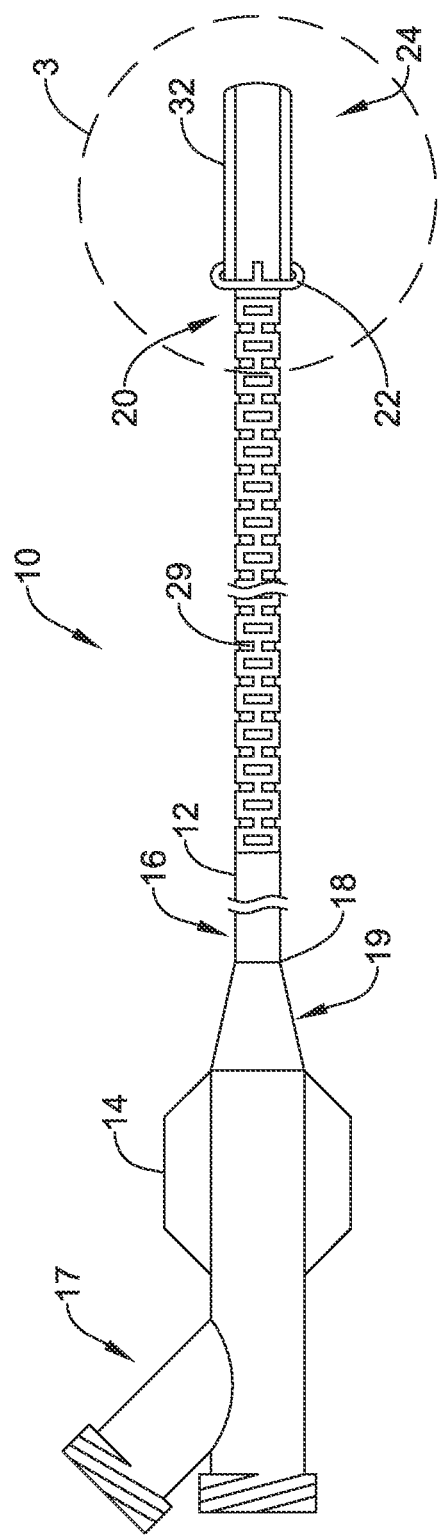
FIG. 1 is a side plan view of a catheter in accordance with various embodiments of the present disclosure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 shows an exemplary catheter 10 in accordance with various embodiments of the present disclosure. In some cases, the catheter 10 may be a guide or diagnostic catheter 10, and may have a length and an outside diameter appropriate for its desired use, for example, to enable intravascular insertion and navigation. For example, when the catheter 10 is adapted as a guide catheter, the catheter 10 may have a length of about 20 centimeters (cm)-250 cm and an outside diameter of approximately 1 French-10 French, depending upon the desired application. In some cases, the catheter 10 may be a microcatheter that is adapted and/or configured for use within small anatomies of the patient. For example, the catheter 10 may be used to navigate to targets sites located in tortuous and narrow vessels such as, for example, to sites within the neurovascular system, certain sites within the coronary vascular system, or to sites within the peripheral vascular system such as superficial femoral, popliteal, or renal arteries. In some cases, the target site is a neurovascular site and may be located within a patient's brain, which is accessible only via a tortuous vascular path. However, it is contemplated that the catheter may be used in other target sites within the anatomy of a patient. An exemplary catheter that may be utilized in accordance with the various embodiments as described herein is shown and described in U.S. Pat. No. 8,182,465, which is incorporated herein by reference in its entirety for all purposes. Additionally, although depicted as having a generally circular cross-sectional shape, it will be understood that the shaft 12 can have other cross-sectional shapes or combinations of shapes without departing from the spirit of the disclosure. For example, the cross-sectional shape of the generally tubular shaft 12 may be oval, rectangular, square, triangular, polygonal, and the like, or any other suitable shape, depending upon the desired characteristics.

As shown in FIG. 1, the catheter 10 can include an elongate catheter shaft 12 including a proximal portion 16 having a proximal end 18 and distal portion 20 having a distal end 22. In some cases, a manifold 14 may be connected to the proximal end 18 of the elongate shaft 12. The manifold may include a hub 17 and/or other structures to facilitate connection to other medical devices (e.g., syringe, stopcocks, Y-adapter, etc.) and to provide access to one or more lumens defined within the elongate shaft 12. In some cases, the hub 17 may be a bifurcated hub, but this is not required. The manifold 14 may also include a strain relief portion adjacent the proximal end 18 of the catheter shaft 12.

In some cases, the shaft 12 may include additional devices or structures such as inflation or anchoring members, sensors, optical elements, ablation devices or the like, depending upon the desired function and characteristics of the catheter 10. In some cases, the catheter 10 may include a detachable tip assembly 24, as will be described in greater detail herein, coupled to the distal end 22 of the catheter shaft 12 that, when detached from the shaft 12, may be used to occlude a vessel. For example, the detachable tip assembly 24 may include an inflatable balloon 32 that may be inflated and used to occlude a vessel at a target site within a patient's body. The balloon 32 may be inflated during release of the detachable tip assembly 24 from the distal end 22 of the catheter shaft, and may remain inflated upon deployment of the detachable tip assembly 24 at the target site within the patient's body.

Figure 2:
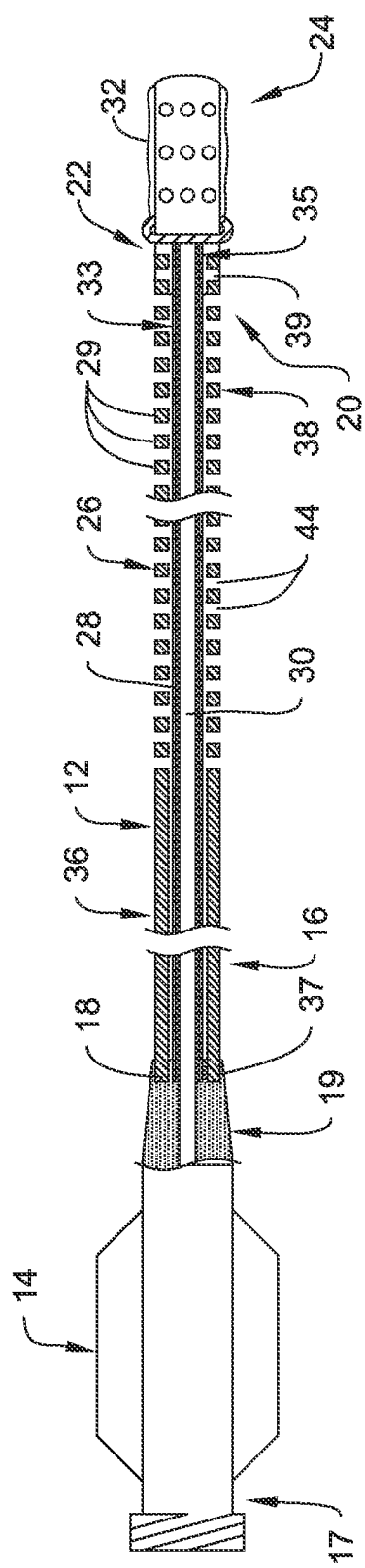
FIG. 2 is a side, cross-sectional view of the catheter shown in FIG. 1 in accordance with various embodiments of the present disclosure.

FIG. 2 is a partial, cross-sectional view of the catheter 10 shown in FIG. 1. As shown in FIG. 2, the shaft 12 can include an outer reinforcing member 26 disposed over an inner tubular member or liner 28 defining at least one lumen 30. In some cases, the reinforcing member 26 can be a generally tubular member including a proximal region 36 having a proximal end 37 and a distal region 38 having a distal end 39. The reinforcing member 26 can be disposed about at least a portion of the inner tubular member 28 at a location along the length of the shaft 12 between proximal end 18 and distal end 22. The length of the reinforcing member 26 may vary depending upon, for example, the length of the shaft 12, the desired characteristics and functions of the catheter 10, and other such parameters. In some cases, as shown in FIG. 2, the reinforcing member 26 has a length such that it may be disposed over the majority of the length of the inner tubular member 28. In addition, the reinforcing member 26 has an inner diameter that is greater than the outer diameter of the inner tubular member 28. As such, in some cases, the reinforcing member 26 can be disposed about the inner tubular member 28 (i.e. a portion of the inner tubular member 28 is disposed within the lumen of the reinforcing member) such that a space or gap is defined between at least a portion of the outer surface of the inner tubular member 28 and the inner surface of the reinforcing member 26.

In many cases, the reinforcing member 26 can be adapted and/or configured to have a desired level of stiffness, torqueability, flexibility, bendability, and/or other characteristics. The desired stiffness, torqueability, flexibility, bendability, or other such characteristics of the reinforcing member 26 can be imparted or enhanced by the structure of the reinforcing member 26. For example, the reinforcing member 26 may include a thin wall tubular structure, including a plurality of apertures 44, such as grooves, cuts, slits, slots, or the like, formed in a portion of, or along the entire length of the tubular reinforcing member 26. Such structure may be desirable because it may allow reinforcing member 26, or portions thereof, to have a desired level of lateral flexibility as well as have the ability to transmit torque and pushing forces from the proximal region 36 to the distal region 38. The apertures 44 can be formed in the reinforcing member using any number of methods known to those of skill in the art. In some cases, the structure of the reinforcing member 26 is formed by cutting and/or removing portions of the tube to form apertures 44. The number, spacing, location, arrangement, and/or orientation of the apertures 44 can be varied to achieve the desired characteristics. In some cases, the apertures 44 may be formed such that one or more spines or beams 29 are formed in the tubular reinforcing member 26 (FIG. 1). In some cases, such spines or beams 29 can include portions of the tubular reinforcing member 26 that remain after the apertures 44 are formed in the body of the tubular member. Such spines or beams 29 may act to maintain a relatively high degree of torsional stiffness, while maintaining a desired level of lateral flexibility.

In addition to, or as an alternative to the structure of the reinforcing member 26, the materials selected for reinforcing member 26 may be chosen so that it has the desired characteristics. For example, reinforcing member 26 may be formed of materials having a desired modulus of elasticity. The reinforcing member 26 may be formed of any materials suitable for use, dependent upon the desired properties of the catheter 10. Some examples of suitable materials include metals, metal alloys, polymers, or the like, or combinations or mixtures thereof. In some cases, the reinforcing member 26 may be fabricated from nitinol tubing to achieve the desired characteristics. Additionally, the reinforcing member 26 may be of, incorporate, or be coated, plated, or clad with a radiopaque or MRI safe imaging material to facilitate radiographic visualization or MRI safe imaging.

As shown in FIG. 2, the inner tubular member 28 can extend from a point within the distal portion 20 to a point within the proximal portion 16 of the catheter shaft 12. The length of the inner tubular member 28 may vary, depending upon, for example, the length of the shaft 12, the desired characteristics and functions of the catheter 10, and other such parameters. In some cases, the inner tubular member 28 can extend substantially the entire length of the shaft 12. In some embodiments, the inner tubular member 28 can include a proximal portion 33 and a distal portion 35. The distal portion 35 of the inner tubular member 28 may be any portion of the inner tubular member 28 that is extends in a distal direction beyond a distal end 39 of the reinforcing member 26, while the proximal portion 33 can be any portion of the inner tubular member 28 that is disposed within, or is proximal to the distal end 39 of reinforcing member 26. In some cases, the distal portion 35 of the inner tubular member 28 may extend beyond a distal end 39 of the reinforcing member 26 and into the distal tip assembly 24.

In some cases, the inner tubular member 28 may be multi-layered to such that the inner tubular member 28 has a desired shapeability, flexibility, steerability, atraumatic characteristics, and/or the like to facilitate navigation through tortuous vascular pathways. For example, in some cases, a distal region of the inner tubular member 28 may include an inner reinforcement layer such as a coil, braid or the like and an outer layer, such as, for example, a polymer sleeve or layer, disposed about the reinforcement layer of the distal region of the inner tubular member 28. Alternatively, the reinforcing coil or braid may be embedded within a polymer sleeve or disposed between multiple layers. In other cases, the inner tubular member 28 may be multi-layered along a majority of its length, and may include an inner reinforcement layer such as a coil, braid or the like and an outer layer, such as, for example, a polymer sleeve or layer, disposed about the reinforcement layer. In other cases, the inner tubular member 28 may be a braided tubular member and may be fabricated from polytetrafluoroethylene (PTFE) or other similar material.

As shown in FIG. 2, the inner tubular member 28 may define at least one lumen 30. In some cases, the inner tubular member 28 may include two lumens. For example, the inner tubular member 28 may include a first lumen for facilitating the passage of one or more guidewires and/or the injection of a contrast fluid and or saline, and a second lumen for delivering pressurized liquid such as, for example, an inflation fluid to a balloon 32 disposed over the detachable tip assembly 24. However, for the ease of illustration, only a single lumen 30 is shown in the figure. It will be generally understood by those skilled in the art that the inner tubular member 28 may include any number of lumens, and in the case of multiple lumens, that the lumens may have different diameters and/or cross-sectional shapes. In some cases, the lumen 30 of the inner tubular member 28 may be in fluid communication with a lumen of the detachable tip assembly 24 such that inflation medium is able to flow through the catheter shaft and into the detachable tip assembly 24, causing balloon 32 to inflate.

Figure 3:
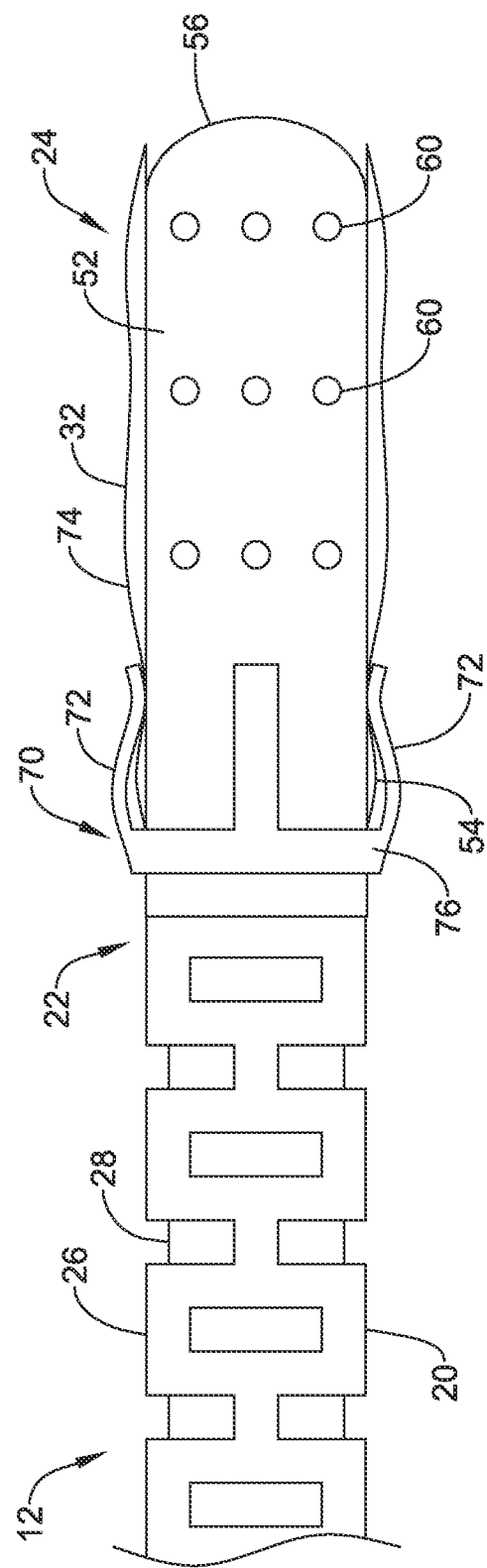
FIG. 3 is close-up, schematic view of a distal tip assembly coupled to a distal portion of the catheter shown in FIG. 1 in accordance with an embodiment of the present disclosure.
Figure 4:
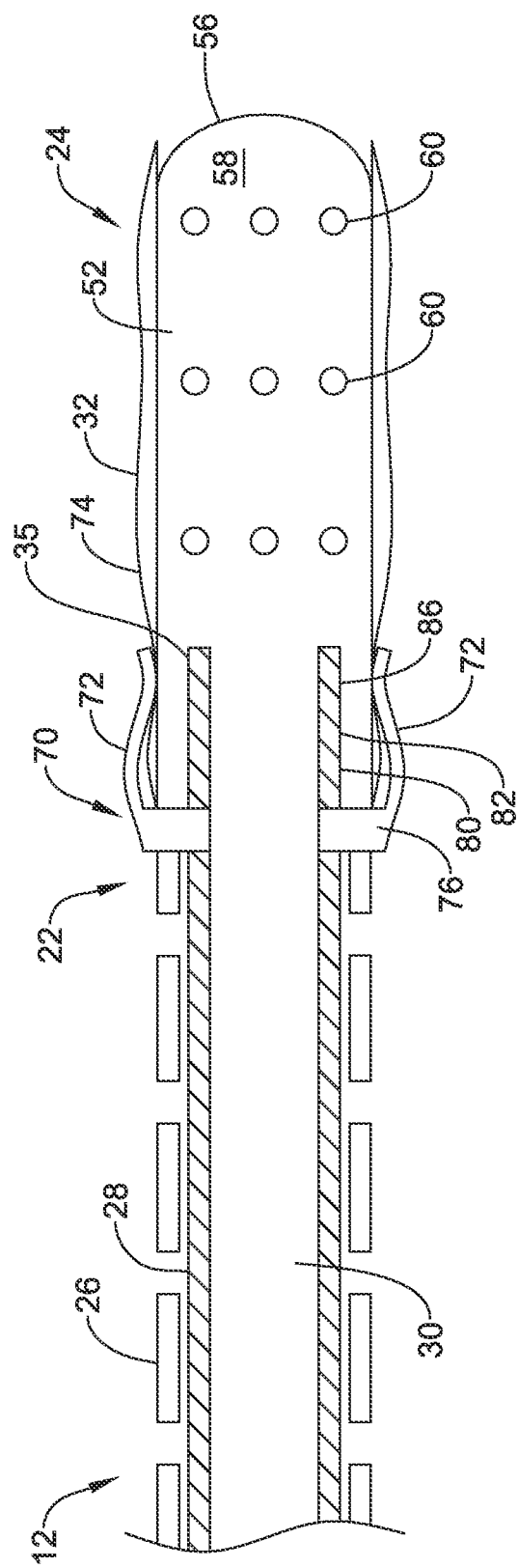
FIG. 4 is a cross-sectional view of the distal tip assembly coupled to the distal portion of the catheter shown in FIG. 3.

FIG. 3 is a close-up schematic view of the detachable distal tip assembly 24 coupled to a distal portion 20 of the catheter shaft 12. FIG. 4 is a cross-sectional view of the detachable tip assembly 24 coupled to the distal portion 20 of the catheter shaft 12 shown in FIG. 3. In some cases, the detachable tip assembly 24 includes an inflatable balloon 32 such that when the balloon 32 is inflated and the distal tip assembly 24 is detached from the catheter shaft 12, the distal tip assembly 24 forms an occlusion device at a target site within a patient's body such as, for example, a blood vessel.

The balloon 32 may be fabricated from any compliant material suitable for use within the human body. In one example, the balloon may be fabricated from polyethylene terephthalate (PET). In some cases, the balloon 32 may be configured to inflate from a collapsed configuration suitable for delivery to the target site, within the body lumen or vessel, as shown in FIGS. 3 and 4, to an expanded configuration. In the expanded configuration, the balloon 32 may be sized such that the balloon 32 contacts the inner walls of the body vessel or lumen in which the distal tip assembly is deployed. The balloon 32 may be inflated until it contacts and engages the inner walls of the vessel in which it is deployed such to form a fluid tight seal, occluding the vessel. In some cases, because it is fabricated from a compliant material, the inflatable balloon 32 may be capable of conforming to the features of the inner surfaces of the vessel in which it is deployed.

As shown in FIGS. 3 and 4, the balloon 32 may be disposed over and attached to a tubular member 52 which also forms a portion of the distal tip assembly 24. In one example, the balloon 32 may be disposed over and attached to the proximal and distal ends 54, 56 of the tubular member 52. In another example, the balloon 32 may be disposed over the tubular member 52 such that it encloses the distal end 56 of the tubular member 52 and is attached to the proximal end 54 of the tubular member 52.

FIGS. 5 and 6 are perspective views of an exemplary tubular member 52 that may form a portion of the distal tip assembly 24 as shown in any one of FIGS. 1-4. In many cases, the tubular member 52 may be fabricated from nitinol tubing. Tubular member 52 may define a lumen 58 and may include an open proximal end 54 (shown in FIGS. 4-6) for receiving an inflation fluid and a sealed distal end 56. In some cases, as shown in FIG. 4, when the distal tip assembly 24 is coupled to the distal end 22 of the catheter shaft 12, the lumen 58 of the tubular member 52 can be in fluid communication with lumen 30 of the inner tubular member 28 such that inflation medium may flow through lumen 30 of the inner tubular member 28 and into the lumen 58 of tubular member 52 of the distal tip assembly 24. In addition, tubular member 52 may include a plurality of apertures 60 formed therein. The apertures 60 may be formed in the tubular member 52 such that they extend through the tubular member 52 from an inner surface 62 to an outer surface 66 to allow the passage of a fluid there through and into balloon 32, causing balloon 32 to inflate. In some cases, the plurality of apertures 60 may be evenly distributed about an outer circumference of the tubular member 52 to facilitate an even flow of fluid from out of the tubular member 52 and into the balloon 32, which may facilitate an even and controlled inflation of balloon 32. The apertures 60 may have any shape that may facilitate fluid flow. In one example, the apertures 60 may be circular. In other cases, the apertures 60 may be rectangular slots or slits formed in the tubular member 52.

Figure 6A:
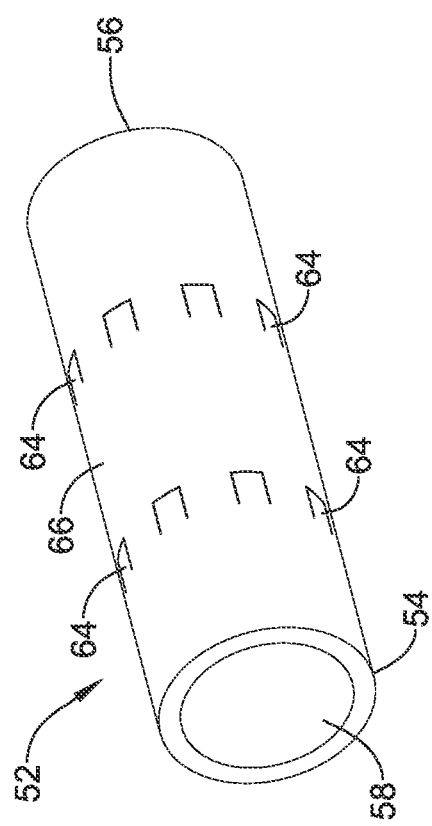
FIGS. 6A and 6B are perspective views of a tubular member that forms a portion of a distal tip assembly in accordance with an embodiment of the present disclosure.
Figure 6B:
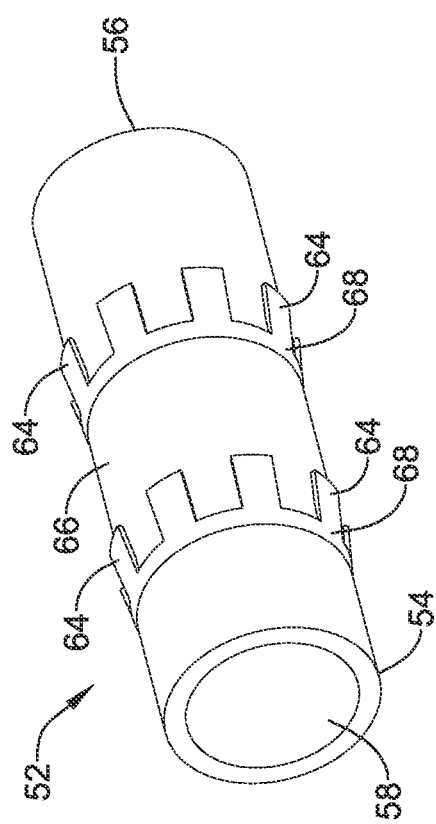

In some cases, to maintain inflation of the balloon 32 upon detachment of the distal tip assembly 24, the apertures 60 may be configured such they can be opened upon the introduction of an inflation fluid into the tubular member 52 and closed upon the cessation of fluid flow into the tubular member 52. For example, as shown in FIGS. 6A and 6B, each of the plurality of apertures may have a corresponding flap 64. The flaps 64 can be configured to open upon the introduction of an inflation medium through the apertures 60 and then close, upon the cessation of fluid flow. In some cases, the flaps 64 may be configured to open once the inflation medium has achieved or exceeded a predetermined pressure. If the pressure has not reached a predetermined pressure, the flaps 64 will remain closed effectively sealing the apertures 60. As such, in some cases, the flaps 64 may function as one-way valves and thus, are capable of maintaining inflation of the balloon 32 when the distal tip assembly 24 is deployed in a vessel. The flow of blood or other bodily fluid into the lumen 58 of the tubular member 52 after deployment of the distal tip assembly 24 may be incapable of overcoming the pressure placed on the flaps 64 by the inflation medium contained within the balloon 32, thus the flaps may remain closed when the distal tip assembly 24 is deployed in a vessel, maintaining the desired inflation of the balloon 32.

In some cases, as shown in FIG. 6A, the flaps 64 may be integrally formed from the tubular member 52, or be formed as a unitary structure with the tubular member 52, during the fabrication of apertures 60 such that when the flaps 64 are closed, they are substantially flush with an outer surface 66 of the tubular member 52. In other cases, the flaps 64 may be formed in annular member 68 (Figured 6B) that is then bonded to the outer surface 66 of the tubular member 52 adjacent to the apertures 60 such that the flaps 64 are disposed over the apertures 60 to effectively seal the apertures 60 when there is no fluid flow through the apertures 60. The material used to form the annular member 68 and the flaps 64 may be the same material used to form the tubular member 52 (e.g. nitinol). In another example, the annular member 68 and flaps 64 may be fabricated from different material than was used to fabricate the tubular member 52. For example, the annular member 68 and flaps 64 may be fabricated from a polymeric material or an elastomeric material such as, for example, silicone. Alternatively, the apertures 60 may be sufficiently shaped and sized such that they create sufficient surface tension across the aperture openings when the balloon is inflated with inflation medium so as to prevent the backflow of inflation medium into the tubular member 52.

Alternatively, the apertures 60 may be covered by a polymeric or elastomeric material that has a particular shape or size that is configured to perform as a one-way valve. For example, duckbill, umbrella, dispensing, access, Belleville, cross-slit and dome values made from polymeric or elastomeric materials are all known in the art (e.g., Minivalve, Inc.).

Referring back to FIGS. 3 and 4, the catheter 10 may include a release mechanism 70 coupled to the distal end 22 of the catheter shaft 12. The release mechanism may be used to releasably couple the distal tip assembly 24, including the inflatable balloon 32 disposed over tubular member 52, to catheter 10 for delivery to a target site within a patient's body. In some cases, upon reaching a target site in a vessel, the release mechanism 70 may be configured to release the distal tip assembly 24 upon expansion of the inflatable balloon 32. In some cases, the release mechanism 70 may be secured to an outer surface of the distal portion 35 of the inner tubular member 28 that extends beyond the distal end of the outer reinforcing member 26. In other cases, the release mechanism 70 may be secured to an outer surface of the reinforcing member 26. In still other cases, the release mechanism 70 may be fabricated from the same nitinol tubing piece used to fabricate the reinforcing member 26 such that the release mechanism 70 forms a distal end of the reinforcing member 26.

In some cases, as shown in FIGS. 3 and 4, the release mechanism 70 may include one or more retaining members 72 that are configured to contact and frictionally engage an outer surface 74 of the balloon 32. The one or more retaining members 72 may be supported by an annular ring 76 that may be secured to an outer surface of the inner tubular member 28, an outer surface of the outer reinforcing member 26, or integrally formed with the outer reinforcing member 26, as described herein. In some cases, the one or more retaining members 72 may be integrally formed from the annular ring 76. In other cases, the one or more retaining members 72 may be bonded to or otherwise secured to the annular ring 76. The one or more retaining members 72 may be fabricated from any number of suitable materials including nitinol and elastomeric materials. The retaining members 72 may be fabricated such that they are capable of placing sufficient frictional forces on the distal tip assembly 24 so as to couple and secure the distal tip assembly 24 to the distal end 22 of the catheter shaft, even in the event of movement (linear or rotational) of the device within the vasculature. In addition, the retaining members 72 may be fabricated such that they are sufficiently flexible such that they are capable of flexing outward and away from a longitudinal axis of the catheter 10 and the distal tip assembly 24 upon inflation of the balloon 32. In some case, the retaining members 72 may be flexible clips or clamps.

In some cases, the release mechanism 70 may include a first pair of first and second retaining members 72 that are disposed on opposite sides of the distal tip assembly 24. In some cases, the first and second retaining members 72 may be disposed 180 degrees from one another about an outer circumference of the distal tip assembly 24. The release mechanism 70 may also include a second pair of third and fourth retaining members 72 (of which one retaining member 72 is shown in FIG. 3) which may be spaced away from the first pair of retaining members and also disposed on opposite sides of the distal tip assembly 24. In some cases, the second pair of retaining members may be spaced about 90 degrees away from the first pair of retaining members and located about 180 degrees opposite from one another about an outer circumference of the distal tip assembly such that each of the four retaining members maybe located approximately 90 degrees from one another about an outer circumference of the distal tip assembly 24. As can be seen in FIGS. 3 and 4, when the distal tip assembly 24 is coupled to the distal end 22 of the shaft 12, the retaining members 72 contact and engage the outer surface 74 of the inflatable balloon 32 and consequently, the tubular member 52 over which the balloon 32 is disposed, so as to secure the detachable tip assembly 24 to the distal end 22 of the catheter shaft 12 for delivery to a target site within a body lumen or vessel.

In some cases, as described herein and as shown in FIG. 4, a distal portion 35 of the inner tubular member 28 of the catheter shaft 12 may extend into the distal tip assembly 24 such that the lumen 30 of the catheter shaft 12 is in fluid communication with the lumen 58 of the tubular member 52 of the distal tip assembly 24. Inflation fluid may be introduced into the lumen 30 via a fluid introduction port located in the hub 17 of the catheter shaft 12. The inflation fluid may flow through the lumen 30 of the catheter shaft 12 defined by inner tubular member 28 and into lumen 58 of the tubular member 52 of the distal tip assembly 24 where it then passes through apertures 60 and into balloon 32 to inflate the balloon 32.

In some cases, the distal portion 35 of the inner tubular member 28 may be disposed within the tubular member 52 of the distal tip assembly 24 such that the outer surface 80 of the inner tubular member 28 contacts an inner surface 82 of the tubular member 52 of the distal tip assembly 24. Passage of fluid through the distal portion 35 of the inner tubular member 28 and into the lumen 58 of the tubular member 52 may cause a radial outward expansion of the distal portion 35 such that the outer surface 80 of distal portion 35 presses up against the inner surface 82 of the tubular member 52 forming a temporary seal 86 between the distal portion 35 of the inner tubular member 28 and the tubular member 52. In some cases, the distal portion 35 of the inner tubular member 28 may be fabricated from a soft plastic material such as, for example, PEBAX, or silicone, that facilitates its radial outward expansion upon passage of a fluid therethrough. The distal portion 35 continues to increase the radial outward expansion forces placed on the inner surface 82 of the tubular member 52 during inflation of the balloon 32 which may further improve the seal 86 between the inner tubular member 28 and the tubular member 52 of the distal tip assembly 24. The temporary seal 86 formed between the outer surface 80 of the distal portion 35 of the inner tubular member 28 and the inner surface 82 of the tubular member 52 may aid in retaining the distal tip assembly 24 on the distal end 22 of the catheter shaft 12 after the balloon 32 has been inflated to a predetermined size to effect release of the balloon from the release mechanism 70. In some cases, after the release mechanism 70 has disengaged from the balloon 32, the balloon 32 may continue to be expanded so as to achieve a size sufficient to occlude the vessel in which the distal tip assembly 24 is deployed. So long as fluid is flowing through the distal portion 35 of the inner tubular member 28 and into the tubular member 52 of the distal tip assembly 24, the distal tip assembly 24 may still be retained on the distal end 22 of the catheter shaft 12 even after the release mechanism 70 has disengage from the distal tip assembly 24. Once the balloon 32 is determined to have reached a size sufficient to occlude the vessel in which the distal tip assembly 24 is deployed, the pressure inside the catheter shaft 12 may be released by the cessation of fluid flow, and the temporary seal 86 formed between outer surface 80 of the distal portion 35 of the inner tubular member 28 and the inner surface 82 of the tubular member 52 may be released, facilitating withdrawal of the inner member from the distal tip assembly 24 and final detachment of the distal tip assembly 24 from the catheter shaft 12.

Figure 7A:
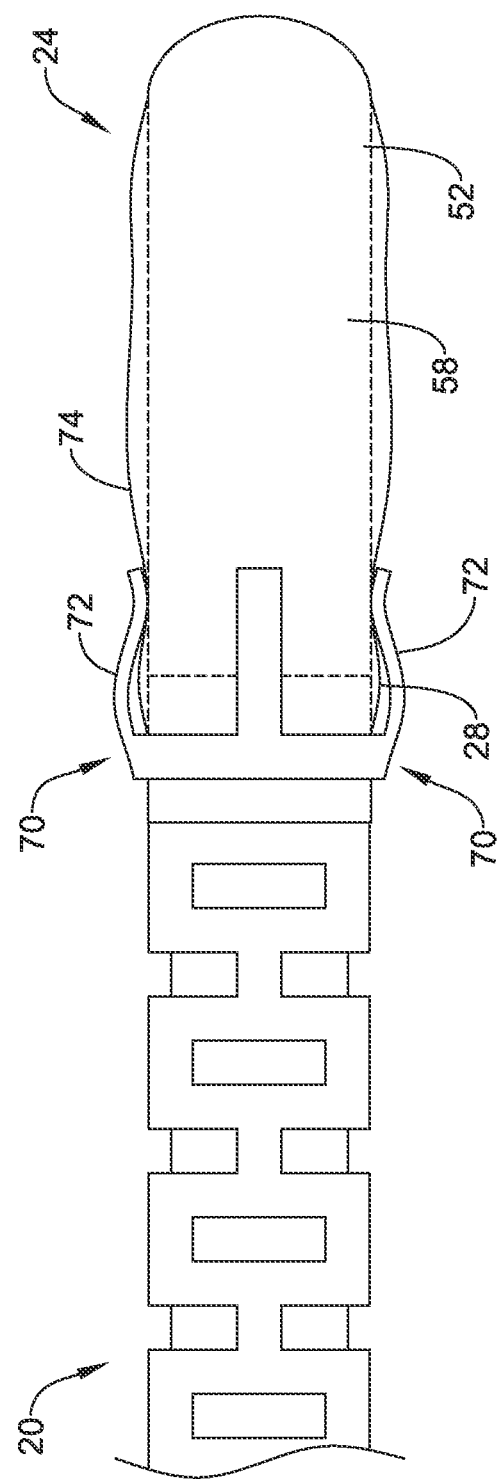
Figure 7B:
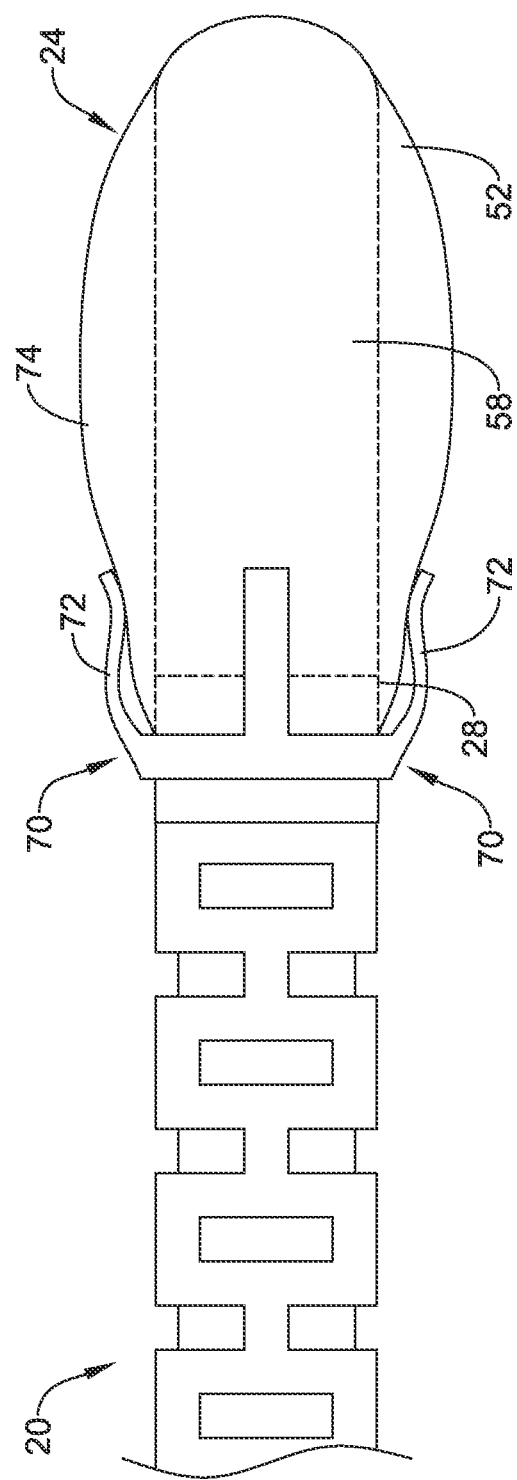

FIGS. 7A-7C is schematic views of a distal tip assembly, as described herein, during different states of detachment from a distal end 22 of a catheter shaft 12. FIG. 7A shows the distal tip assembly 24 during delivery of the distal tip assembly 24 to a target site within a body vessel or lumen prior to introduction of an inflation medium into the balloon 32. During advancement of the distal portion 20 of the catheter 10 at a target site within a body lumen or vessel, the balloon 32 may be in a collapsed configuration until the target site is reached. As shown in FIG. 7A, the retaining members 72 may be in contact with and frictionally engage the outer surface 74 of the balloon 32 and consequently, the tubular member 52 of the distal tip assembly 24 to retain the distal tip assembly 24 on the distal end 22 of the catheter 10 during delivery. Upon reaching the target site, an inflation medium may be introduced into a fluid delivery port located in the manifold 14 of the catheter 10 (FIG. 1). The inflation medium may flow through the lumen 30 of the catheter shaft 12 defined by inner tubular member 28 and into lumen 58 of the tubular member 52 of the distal tip assembly 24 where it then passes through apertures 60 and into balloon 32 to inflate the balloon 32. FIG. 7B shows the balloon 32 in a partially expanded configuration during inflation of the balloon 32. As can be seen in FIG. 7B, the retaining members 72 are configured to flex outward and away from a longitudinal axis of the catheter 10 and the distal tip assembly 24 during inflation of the balloon 32. Upon expansion of the balloon 32 to a predetermined size, the retaining members 72 may be configured to disengage from the balloon 32 and consequently, from the distal tip assembly 24, causing the distal tip assembly 24 to detach from the distal end 22 of the catheter shaft. In some cases, additional fluid may continue to be delivered to the balloon 32 to continue to inflate the balloon to a size sufficient to achieve occlusion of the body vessel or lumen. The introduction of fluid is then ceased, causing any seal formed between the inner tubular member 28 of the catheter shaft 12 and the tubular member 52 of the distal tip assembly further effecting detachment of the distal tip assembly 24 from the distal end 22 of the catheter shaft 12, as shown in FIG. 7C. After the distal tip assembly 24 has been deployed at the target site within the body vessel or lumen, the catheter 10 may be withdrawn from the patient's body.

Figure 8A:
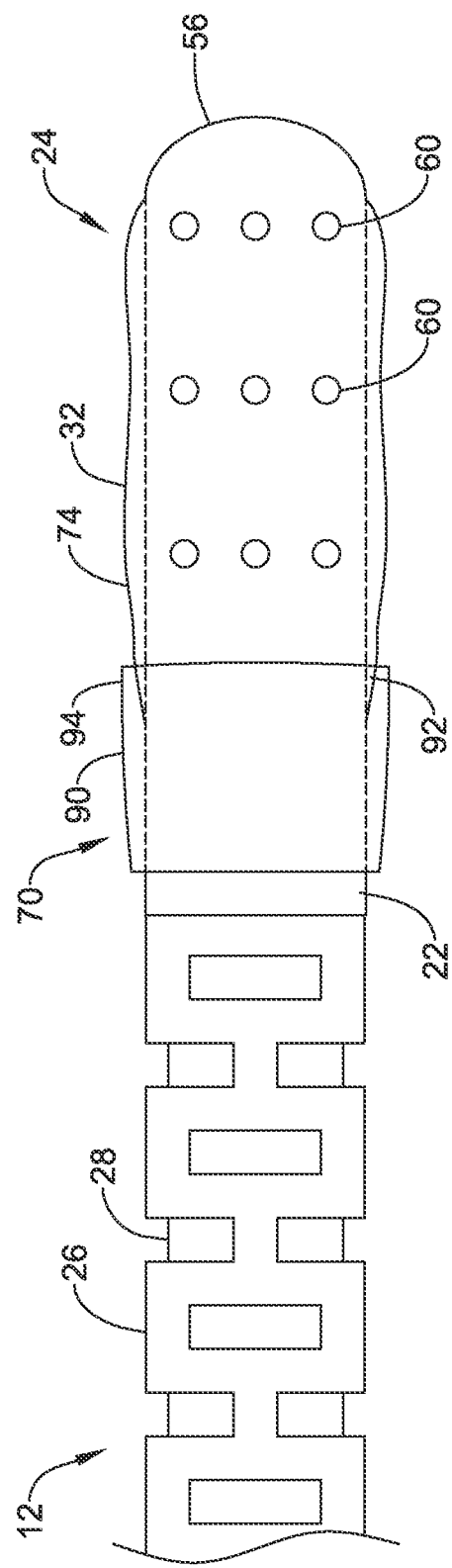
FIGS. 8A and 8B are close-up, schematic view of a distal tip assembly coupled to a distal portion of the catheter in accordance with another embodiment of the present disclosure.
Figure 8B:
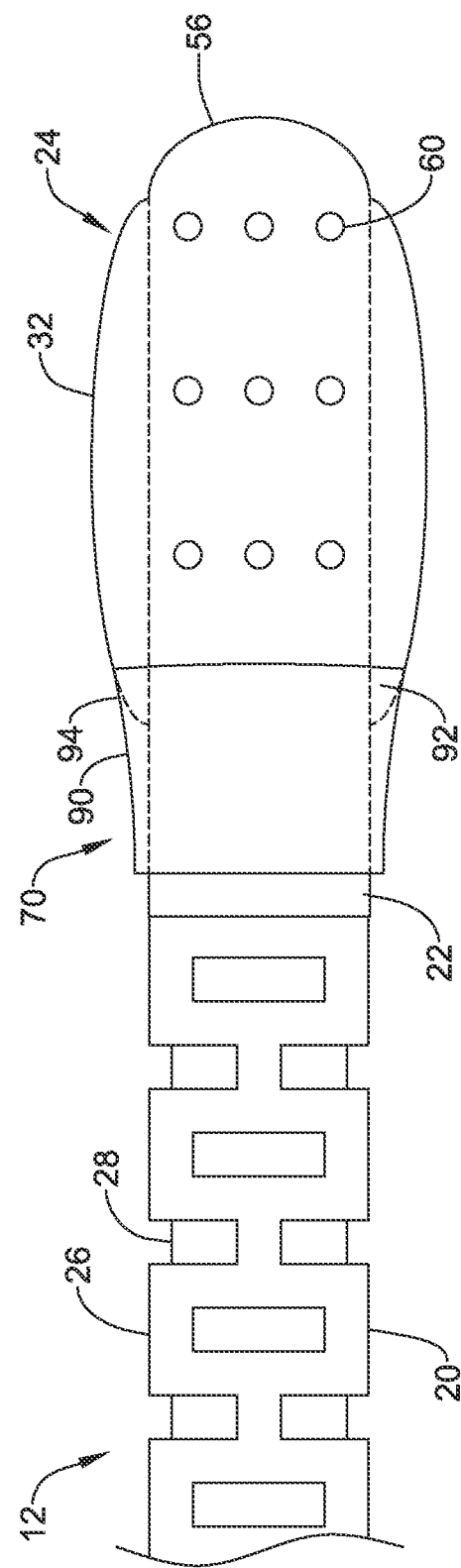

In other cases, as shown in FIGS. 8A and 8B, the release mechanism 70 may include a tubular segment 90 that may be disposed over the distal end 22 of the catheter shaft 12 and a proximal portion 92 of the inflatable balloon 32 so as to releasably couple the distal tip assembly 24 to the distal end 22 of the catheter. The tubular segment 90 may be disposed over the outer surface of the reinforcing member 26 or the outer surface of the distal portion 35 of the inner tubular member 28 which extends beyond the distal end of the reinforcing member. In either example, the tubular segment 90 may have a minimal wall thickness such that it maintains it a low profile when disposed on the catheter shaft 12. In some cases, the tubular segment 90 may be fabricated from a material having sufficient flexibility such that at least the distal portion of the tubular segment 90 is capable of expanding as balloon 32 inflates, as shown in FIG. 8B. Exemplary materials that may be used to fabricate the tubular segment 90 may include, but are not limited from PEBAX, polyethylene terephthalate (PET), silicone, a polyurethane and/or the like. In some cases, at least the distal portion 94 of the tubular segment 90 may be configured to expand to a predetermined outer diameter as the balloon 32 inflates, whereupon reaching the pre-determined out diameter, the tubular segment 90 may be configured to release the balloon 32 and consequently, the distal tip assembly 24. In some cases, the balloon 32 may continue to be inflated after release by the tubular segment 90 until it has reached a size sufficient to occlude the vessel in which the distal tip assembly is deployed. After the balloon 32 has been released, the tubular segment 90 may be configured to return to an initial, non-expanded outer diameter, as shown in FIG. 8A, to facilitate withdrawal of the catheter 10 from the patient's body.

Figure 9:
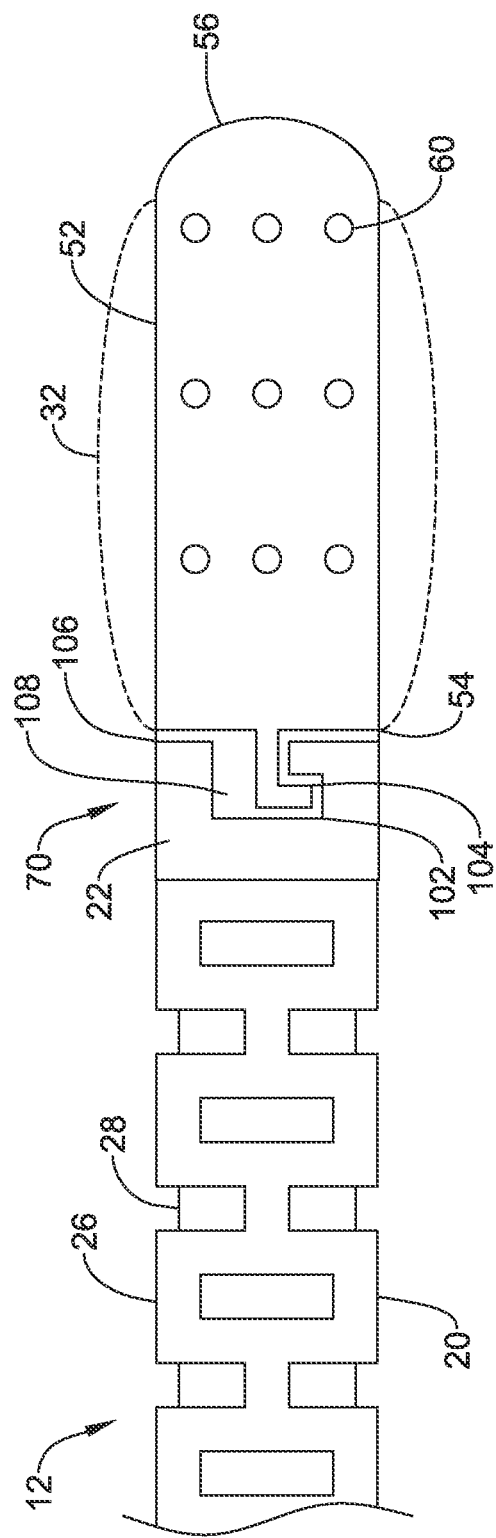
FIG. 9 is close-up, schematic view of a distal tip assembly coupled to a distal portion of the catheter in accordance with another embodiment of the present disclosure.

In yet another example, as shown in FIG. 9, the release mechanism 70 may include at least one pair of interlocking features 102, 104 that may be configured to releasably couple the distal tip assembly 24 to the distal end 22 of the catheter shaft 12. In some cases, a first locking feature 102 may be formed within an annular member 106 and a second locking feature 104 may be coupled to or integrally formed with the proximal end 54 of the tubular member 52 of the distal tip assembly 24. The annular member 106 may be may be disposed over the outer surface of the reinforcing member 26 or the outer surface of the distal portion 35 of the inner tubular member 28 which extends beyond the distal end of the reinforcing member. The first and second locking features 102, 104 may be configured to cooperate with one another to releasably attach the proximal end 54 of the tubular member 52 to the distal end 22 of the catheter shaft. In some cases, the first locking feature 102 may be a recess formed within the annular member 106 having a shape corresponding to the shape the second locking feature 104, which extends away from the proximal end 54 of the tubular member 52. Additionally, a channel 108 may be formed within the annular member adjacent the first locking feature 102 such that it facilitates detachment of the distal tip assembly 24 from the catheter shaft 12 via rotation of the catheter shaft. In some cases, the release mechanism 70 may include a second pair of interlocking features (not shown) located approximately 180 degrees opposite the first pair of interlocking features 102, 104 about an outer circumference of the catheter 10.

In use, after inflation of the balloon 32, a clinician may twist or apply torque to the proximal end of the catheter which is then transferred down the catheter shaft 12 to cause release of the mechanical interlock between the first and second locking feature 102, 104. An example of such a torqueable catheter is Boston Scientific's Direxion torqueable microcatheter. Inflation of the balloon 32 prior to release of the release of the first and second locking features 102, 104, may place enough of a resistive force on the release mechanism 70, such that the clinician may be able to push the distal end 22 of the catheter shaft 12 forward as torque is applied to effectively cause the locking features 102, 104 to disengage from one another.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A medical device, comprising:
   a main catheter body extending from a proximal end to a distal end;
   a distal tip assembly releasably coupled to the distal end of the main catheter body, the distal tip assembly including a tubular member defining a lumen extending from a proximal end to a distal end, and an inflatable balloon disposed over and secured to the tubular member;
   an inflation lumen in fluid communication with the inflatable balloon; and
   a release mechanism at the distal end of the main catheter body, the release mechanism comprising a tubular segment engaging an outer surface of the inflatable balloon when the distal tip assembly is coupled to the distal end of the main catheter body prior to deployment, wherein the tubular segment is configured such that expansion of the inflatable balloon expands at least a distal portion of the tubular segment outward and away from the main catheter body until the distal tip assembly including the inflatable balloon is released from the main catheter body.

2. The medical device of claim 1, wherein the main catheter body comprises an outer member disposed over an inner tubular member.

3. The medical device of claim 2, wherein the outer member comprises a nitinol tube having a plurality of apertures defined therealong.

4. The medical device of claim 2, wherein the inner tubular member defines the inflation lumen.

5. The medical device of claim 2, wherein a distal portion of the inner tubular member extends within the lumen defined by the tubular member of the distal tip assembly.

6. The medical device of claim 1, wherein the lumen of the tubular member of the distal tip assembly is in fluid communication with the inflation lumen.

7. The medical device of claim 6, wherein the tubular member includes a plurality of apertures formed in an outer surface thereof, and the inflation lumen is in fluid communication with the inflatable balloon through the apertures.

8. The medical device of claim 7, wherein each of the plurality of apertures formed in the tubular member of the distal tip assembly comprises a corresponding flap disposed over the apertures, wherein when an inflation fluid is introduced into the tubular member the flaps move outward and away from the outer surface of the tubular member to facilitate passage of the fluid therethrough to inflate the balloon, and wherein after the balloon is inflated, the flaps close the apertures and maintain inflation of the balloon.

9. The medical device of claim 1, wherein a proximal end and a distal end of the balloon is attached to the proximal end and the distal end of the tubular member such that the balloon has a substantially cylindrical shape upon inflation.

10. The medical device of claim 1, wherein the distal end of the tubular member of the distal tip assembly is sealed.

11. The medical device of claim 1, wherein the tubular segment is designed to release the distal tip assembly upon inflation of the inflatable balloon to a predetermined size.

12. A medical device, comprising:
- a main catheter body extending from a proximal end to a distal end;
- a distal tip assembly releasably coupled to the distal end of the main catheter body, the distal tip assembly including a tubular member defining a lumen extending from a proximal end to a distal end, and an inflatable balloon disposed over and secured to the tubular member;
- an inflation lumen in fluid communication with the inflatable balloon; and
- release mechanism comprising a first locking feature associated with the distal end of the main catheter body, and a second locking feature associated with the proximal end of the distal tip assembly, wherein the distal tip assembly is releasably coupled to the main catheter body by mating surfaces of the first and second locking features prior to deployment, wherein the first and second locking features are configured such that upon rotation of the main catheter body relative to the distal tip assembly, the mating surfaces of the first and second locking features disengage to release the distal tip assembly from the main catheter body.

13. The medical device of claim 12, wherein the first locking feature includes a recessed portion configured to receive a corresponding projection of the second locking feature.

14. The medical device of claim 12, wherein the main catheter body is rotatable relative to the distal tip assembly and the first and second locking features are disengageable only after expansion of the inflatable balloon.

15. The medical device of claim 12, wherein the tubular member includes a plurality of apertures formed in an outer surface thereof, and the inflation lumen is in fluid communication with the inflatable balloon through the apertures.

16. The medical device of claim 15, wherein each of the plurality of apertures formed in the tubular member of the distal tip assembly comprises a corresponding flap disposed over and sealing the apertures, wherein when an inflation fluid is introduced into the tubular member the flaps move outward and away from the outer surface of the tubular member to facilitate passage of the fluid therethrough to inflate the balloon, and wherein after the balloon is inflated, the flaps close to seal the apertures and maintain inflation of the balloon.

17. The medical device of claim 12, wherein a proximal end and a distal end of the balloon is attached to the proximal end and the distal end of the tubular member such that the balloon has a substantially cylindrical shape upon inflation.

18. A method of delivering an occlusion device to a target location within a body lumen, the method comprising:
- advancing a catheter assembly to a target location within a body lumen, the catheter assembly comprising:
  - a main catheter body extending from a proximal end to a distal end,
  - a distal tip assembly releasably coupled to the distal end of the main catheter body, the distal tip assembly including an inflatable balloon disposed over an outer surface of the distal tip assembly,
  - an inflation lumen extending within the main catheter body, and
  - a release mechanism comprising a first locking feature associated with the distal end of the main catheter body, and a second locking feature associated with the proximal end of the distal tip assembly;
- inflating the inflatable balloon to at least a predetermined size; and
- rotating the main catheter body relative to the distal tip assembly to release the distal tip assembly.

19. The method of claim 18, further comprising withdrawing the main catheter body from the body lumen.

20. The method of claim 18, wherein the distal tip assembly includes a tubular member defining a lumen extending from a proximal end to a sealed distal end, the tubular member including a plurality of apertures formed in an outer surface thereof, and the inflation lumen is in fluid communication with the inflatable balloon through the apertures.

* * * * *